(12) United States Patent
Helmer et al.

(10) Patent No.: US 9,084,852 B2
(45) Date of Patent: *Jul. 21, 2015

(54) PISTON ROD ASSEMBLY FOR A DRUG DELIVERY DEVICE

(75) Inventors: Michael Helmer, Frankfurt am Main (DE); Christoph Eisengarthen, Dexheim (DE); Winfried Huthmacher, Frankfurt (DE); Carsten Mosebach, Mainz (DE); Leo Zeimetz, Buttelborn (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 293 days.

This patent is subject to a terminal disclaimer.

(21) Appl. No.: 13/582,568

(22) PCT Filed: Mar. 31, 2011

(86) PCT No.: PCT/EP2011/054986
§ 371 (c)(1),
(2), (4) Date: Nov. 27, 2012

(87) PCT Pub. No.: WO2011/121061
PCT Pub. Date: Oct. 6, 2011

(65) Prior Publication Data
US 2013/0066279 A1 Mar. 14, 2013

Related U.S. Application Data

(63) Continuation-in-part of application No. 12/791,499, filed on Jun. 1, 2010, now Pat. No. 8,986,259.

(30) Foreign Application Priority Data

Mar. 31, 2010 (EP) ..................................... 10158613

(51) Int. Cl.
*A61M 5/315* (2006.01)
*A61M 5/24* (2006.01)
*A61M 5/31* (2006.01)

(52) U.S. Cl.
CPC ......... *A61M 5/31515* (2013.01); *A61M 5/3156* (2013.01); *A61M 5/3158* (2013.01);

(Continued)

(58) Field of Classification Search
CPC ............ A61M 5/3156; A61M 5/3158; A61M 5/31515; A61M 5/31555; A61M 5/24; A61M 5/3146; A61M 5/31511; A61M 2005/2407; A61M 2005/3152; A61M 2207/00; Y10T 29/49826
USPC ......................................... 604/218, 220, 187
See application file for complete search history.

(56) References Cited

U.S. PATENT DOCUMENTS 2,681,297 A 6/1954 Moore et al.
2,895,474 A * 7/1959 Reznek ......................... 604/228

(Continued)

FOREIGN PATENT DOCUMENTS

| EP | 1923083 | 5/2008 |
| WO | 2009/095332 | 8/2009 |
| WO | 2010/029043 | 3/2010 |

OTHER PUBLICATIONS

European Search Report for European App. No. 10158613, completed Sep. 27, 2010.

(Continued)

*Primary Examiner* — Edelmira Bosques
(74) *Attorney, Agent, or Firm* — McDonnell Boehnen; Hulbert & Berghoff LLP (57) ABSTRACT

The present invention relates to a piston rod assembly for a drug delivery device, comprising: a piston rod adapted to be operably engaged with a piston of a cartridge containing a medicament, at least one adjusting member displaceably disposed at the piston rod with respect to the piston rod's long axis, and being interconnected with a distal end section of the piston rod, and at least one interlock means adapted to interact with the adjusting member and/or with the piston rod for mutually locking in position the adjusting member and the piston rod in an arbitrary relative position in order to compensate for tolerances of manufacture and/or of assembly.

13 Claims, 3 Drawing Sheets (52) U.S. Cl.
CPC ............ *A61M5/31555* (2013.01); *A61M 5/24* (2013.01); *A61M 5/3146* (2013.01); *A61M 5/31511* (2013.01); *A61M 2005/2407* (2013.01); *A61M 2005/3152* (2013.01); *A61M 2207/00* (2013.01); *Y10T 29/49826* (2015.01)

(56) References Cited

U.S. PATENT DOCUMENTS

| | | | |
|---|---|---|---|
| 3,115,135 A * | 12/1963 | Sarnoff | 604/228 |
| 5,308,340 A * | 5/1994 | Harris | 604/208 |
| 2005/0177116 A1 | 8/2005 | Graf | |
| 2006/0129122 A1* | 6/2006 | Wyrick | 604/506 |
| 2011/0245780 A1* | 10/2011 | Helmer et al. | 604/211 |

OTHER PUBLICATIONS

International Search Report for Int. App. No. PCT/EP2011/054986, completed Aug. 25, 2011.

* cited by examiner

PISTON ROD ASSEMBLY FOR A DRUG DELIVERY DEVICE

CROSS REFERENCE TO RELATED APPLICATIONS

The present application is a U.S. National Phase Application pursuant to 35 U.S.C. §371 of International Application No. PCT/EP211/054986 filed Mar. 31, 2011, which claims priority to European Patent Application No. 10158613.9 filed on Mar. 31, 2010 and U.S. patent application Ser. No. 12/791,499 filed Jun. 1, 2010. The entire disclosure contents of these applications are herewith incorporated by reference into the present application.

FIELD OF THE INVENTION

The present invention relates to a piston rod assembly for a drug delivery device that allows a user to select single or multiple doses of an injectable medicinal product and to dispense and to deliver the set dose to a patient, preferably by way of injection. In particular, the present invention relates to such drug delivery devices that are handled by the patients themselves, such like pen-type injectors.

BACKGROUND

Drug delivery devices allowing for multiple dosing of a required dosage of a liquid medicinal product, such as a liquid medicament, and further providing administration of the liquid to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicinal product to be administered is provided in a cartridge that has a moveable piston or bung mechanically interacting with a piston rod of a drive mechanism of the drug delivery device. By applying thrust to the piston in distal direction, a certain amount of the medicinal fluid is expelled from the cartridge and may be administered to the patient by some kind of needle assembly being in fluid communication with the cartridge.

Due to inevitable manufacturing tolerances of the device and the cartridge there may for instance persist axial clearance between a cartridge's piston and the piston rod when the device is finally assembled. Typically, prior to a primary use of the device, an end-user, e.g. a patient has to conduct a so-called set-up of the drive mechanism in order to ensure, that the piston of the cartridge and the piston rod are located at a pre-defined position with respect to each other, thus ensuring, that with an initial dose setting and a subsequent dose dispensing step, a predefined amount of the medicinal product can be disposed in an accurate way. By way of the set-up step, mechanical tolerances of movable components of the drug delivery device can be annihilated.

In particular with disposable drug delivery devices, wherein the entire device is discarded after consumption of the medicament, the device is initially provided with a cartridge containing the medicament. Such disposable but also reusable drug delivery devices are assembled in a mass production process in which for instance two housing components of the drug delivery device receive a cartridge and a drive mechanism including the piston rod, respectively. Then, in a final step of assembly, the two pre-configured housing components or respective sub-assemblies are to be mutually interconnected. When reaching a defined final assembly configuration, it would be beneficial when the piston rod and the piston of the cartridge either mutually abut or when piston and piston rod are separated by a pre-defined gap.

Exact and precise mutual positioning and alignment of piston and piston rod is important and crucial for accurate and reliable functionality of the drug delivery device. Moreover, the piston rod should not exert pressure to the plunger during assembly, which may otherwise result in a rather uncontrolled expelling of the medicament prior to a first use of the drug delivery device when a needle is attached.

Since at least some or even major components of the drug delivery device are designed as plastic injection molded components, the components themselves, and their assembly is inevitably subject to certain geometric tolerances. Moreover, the cartridge itself and in particular the position of the piston within the cartridge may vary.

It is therefore an object of the present invention to provide an improved piston rod assembly for a drug delivery device which may allow compensating for geometric tolerances of the drug delivery device and its components. In a further object, the piston rod assembly and the respective drug delivery device should be intuitive and easy in handling. Furthermore, a general compatibility of the piston rod assembly and of a respective drug delivery device with existing manufacturing processes is a further aim of the invention. Finally, the invention should be implementable with reasonable costs and expenditure.

SUMMARY

In a first aspect, the invention provides a piston rod assembly for a drug delivery device which is adapted to become operably engaged with a piston of a cartridge that is filled with an injectable fluid, in particular with a medicament, such like insulin. The piston rod assembly is intended to become operably engaged with a drive mechanism of a drug delivery device allowing for setting a pre-defined dose and to induce an axial displacement on the piston rod in distal direction in order to move the piston of the cartridge in a respective direction for expelling a pre-defined amount of the medicament.

The piston rod is therefore adapted to be operably engaged with a piston of a cartridge containing a medicament. Mutual engagement of piston rod and piston preferably comprises a unidirectional thrust transferring engagement of piston rod and piston, e.g. through a mutual and releasable abutment. Hence, the piston rod assembly is adapted and intended to move the piston in only one direction. It is therefore sufficient, when respective abutment surfaces of piston rod assembly and piston are of substantially planar geometry. During a typical dispensing procedure, the cartridge itself is in fluid communication with a piercing assembly, such like a needle, a cannula, an infusion tube or with similar delivery devices.

The cartridge itself can comprise a vial or carpule, sealed by means of the movable piston. In alternative embodiments, the cartridge may also comprise a syringe, preferably adapted and designed for a single use.

The piston rod assembly further comprises at least one adjusting member displaceably disposed at the piston rod. The adjusting member is thus connected to the piston rod and can be displaced with respect to the piston rod, preferably along the piston rod's long axis, hence in axial direction. Here, the adjusting member is interconnected with a distal end section of the piston rod facing towards the piston of the cartridge. Consequently, the at least one adjusting member is to be arranged between the piston rod and the cartridge's piston. The adjusting member therefore serves as a kind of interface member intended to reduce and/or to annihilate variations of the mutual distance and/or relative position of piston rod and piston that are for instance due to manufacturing and/or assembly tolerances.

The piston rod assembly further comprises at least one interlock means which is adapted to interact with the adjusting member and/or with the piston rod for mutually locking in position the adjusting member and the piston rod in an arbitrary relative position to each other. In particular, the adjusting member's axial position relative to the piston rod can be continuously modified, preferably for eliminating said manufacturing and assembly tolerances. Once the adjusting member has been positioned in a tolerance-eliminating configuration with the piston rod, its relative position to the piston rod can be either permanently or releasably locked by way of the at least one interlock means.

During a tolerance eliminating procedure, adjusting member and piston rod are mutually displaceable with respect to each other. In other words, they may be telescopically shiftable in axial direction. Once a tolerance-eliminating configuration has been attained, adjusting member and piston rod can be mutually interlocked in such a way, that the piston rod assembly is enabled to transfer a respective thrust to the piston required for displacing the piston in distal direction. By having a piston rod and an adjusting member displaceably attached or connected thereto, the overall axial dimension and extension of the piston rod assembly becomes variable, in particular for the purpose of tolerance elimination.

Furthermore, the adjusting member and the piston rod are threadedly engaged in order to axially displace the piston rod and the adjusting member relative to each other. By way of a threaded engagement of adjusting member and piston rod, the overall axial dimensions of the piston rod assembly can be modified in a continuous way. It is of further benefit when the interlock means is adapted to inhibit self-acting relative rotation of piston rod and adjusting member. Hence, the interlock means prevents, that the adjusting member autonomously rotates with respect to the piston rod and vice versa. By way of the threaded engagement, axially directed forces and thrust can be transferred, e.g. from a drive mechanism via the piston rod to the adjusting member and finally to the piston of the cartridge.

Since the interlock means is designed for inhibiting self-acting relative rotation of piston rod and adjusting member, the interlock means itself may not have to withstand those comparatively large axial forces or respective thrust, which is required to displace the piston of the cartridge in distal direction.

In a further preferred aspect, the adjusting member comprises a threaded receptacle, which is adapted to receive a correspondingly threaded distal socket portion of the piston rod.

In an alternative embodiment, the piston rod comprises a threaded receptacle at its distal end section, which is adapted to receive a correspondingly threaded proximal socket portion of the adjusting member. Hence, the threaded engagement of piston rod and adjusting member can be generally implemented either way.

In another preferred aspect, the interlock means comprises at least one resiliently biased tongue member which is adapted to engage with a corrugated surface portion of the adjusting member or of the piston rod. Preferably, the interlock means may positively engage with a side wall of the receptacle of either the adjusting member or the piston rod. Additionally, the interlock means is preferably arranged on that part or component of the piston rod assembly comprising the socket portion.

In another preferred embodiment, the tongue member is arranged laterally offset with respect to the socket portion. With respect to the transverse plane of the piston rod assembly that extends perpendicular to the piston rod's long axis, the axially protruding socket portion is typically arranged in the centre of the piston or on the centre of the adjusting member. Here, the resiliently biased tongue member is arranged and displaced with a lateral or radial offset with respect to the socket portion. Hence, mutual arrangement of socket portion and tongue member is such that a gap is formed there between adapted to receive a side wall section of the receptacle.

In a further preferred embodiment, the radially inwardly facing side wall section of the receptacle is threaded in order to provide threaded engagement with the correspondingly threaded socket portion. The side wall section of the receptacle at its outwardly facing side is preferably corrugated or comprises a ribbed structure, by way of which a kind of positive or frictional engagement of the receptacle and the tongue member can be established in order to inhibit self-acting relative rotation of the receptacle relative to the socket portion.

In alternative embodiments it is also conceivable, that an outwardly facing side wall section of the receptacle is threaded and wherein an inwardly facing side wall section of said receptacle is corrugated or comprises a ribbed surface structure. In such embodiments, the resiliently biased tongue members are preferably arranged radially inward with respect to the threaded engagement of adjusting member and piston rod.

Mutual engagement and interaction of resiliently biased tongue members and the corrugated surface provides a kind of snap-in feature. Depending on the overall number of longitudinally extending ribs or corrugations and the pitch of the thread a fine adjustment of piston rod and adjusting member in a sub-millimeters range, preferably in a range of $\frac{1}{10}$ mm or even $\frac{1}{100}$-mm can be attained.

In a further preferred embodiment, threaded and corrugated side wall sections of the receptacle are arranged at least partially offset with respect to each other in axial direction. Moreover, the corrugations or the ribs of said wall section comprise an axial extension substantially corresponding with an overall axial extension of the mutually corresponding threads of receptacle and socket portion.

According to a further embodiment, the piston rod comprises at least two tongue members arranged at the piston rod and being axially displaced in proximal direction with respect to the piston rod's distal end section. Here, the tongue members, that are preferably arranged opposite to each other in the transverse plane comprise radially inwardly pointing lug portions that are adapted to engage with the corrugated or ribbed outer side wall section of a proximal end of the adjusting member comprising a cupped receptacle.

In a further aspect, it is intended, that the adjusting member comprises a contact surface at its distal end section that faces towards a proximal end section of the piston if the drug delivery device is in a final assembly configuration. The contact or abutment surface is of substantially plane shape and preferably extends in the transverse plane, hence perpendicular to the axial or longitudinal extension of the piston rod. Preferably, the distally facing outer surface of the cupped receptacle of the adjusting member serves as a contact surface. By way of a substantially planar contact surface, the piston rod assembly and the piston of the cartridge are not to mechanically engaged and may be easily separated on demand, e.g. when an empty cartridge is to be replaced by a filled one. A planar shaped abutment surface also facilitates to establish a gap of predetermined size between the piston rod assembly and the piston if required.

In a final assembly configuration of the drug delivery device, the contact surface of the adjusting member may already abut with a proximal end section of the piston. Hence, during assembly of the drug delivery device, the adjusting member is configured such, that upon reaching the final assembly configuration, the contact surface of the adjusting member gets in direct contact with a proximal end of the piston. The drug delivery device is ready to use when delivered to customers. An initial set-up step for bringing piston rod assembly and piston of the cartridge in abutment with each other is no longer required and becomes superfluous.

Preferably, mutual abutment of piston and piston rod is such, that the piston does not yet apply substantial pressure or thrust to the piston in order to prevent generation of droplet at the distal tip of a needle assembly when assembled to the cartridge. Generally, in this way, the overall device handling can be simplified.

However, in another and alternative embodiment it is also conceivable, that the piston rod assembly is configured during assembly of the drug delivery device in such a way, that a pre-defined gap between adjusting member and piston of the cartridge is attained when the device is in its final assembly configuration. Here, the adjusting member is manipulated during final assembly of the drug delivery device in such a way, that the gap matches with a pre-defined gap size. Set-up of the cartridge may for instance be implemented in the drive mechanism of the drug delivery device. Also here, the end user does not have to conduct or to trigger a set-up step in which piston rod assembly and piston of the cartridge are brought into mutual abutment.

In another independent aspect, the invention further relates to a drug delivery device for dispensing of a dose of a medicament. The drug delivery device comprises a first housing component adapted to receive and to house a cartridge that comprises the medicament, wherein the cartridge comprises a piston slidably arranged therein in an axial direction. By way of the piston, the inner volume of the cartridge is sealed in proximal direction while the cartridge further comprises an outlet, facing in distal direction and which is to be coupled with a piercing element, such like and injection needle or a cannula in a fluid-transferring way.

The drug delivery device further comprises a second housing component which is adapted to house a drive mechanism that comprises a piston rod assembly as described above.

The first and second housing components are further adapted to be interlocked by way of mutually corresponding fastening means, for instance by way of a snap-in feature or otherwise e.g. by way of a threaded engagement. During assembly and in particular before first and second housing components are joined together, the piston rod assembly, which is variable in length, is adapted to modify an axial gap between the piston rod assembly and the piston of a cartridge to a predefined gap size. Depending on the type of drive mechanism, the gap size may equal zero, wherein the piston rod assembly and the cartridge's piston mutually abut upon assembly of first and second pre-configured housing components.

The axial gap size between the piston rod assembly and the piston is modifiable by way of the threaded engagement of the adjusting member and the piston rod in order to axially displace the piston rod and the adjusting member relative to each other. The interlock means is further adapted to inhibit self-acting relative rotation of piston rod and adjusting member. By way of the interlock means, the actual length or axial extension of the piston rod assembly can be fixed.

It is even conceivable, that the interlock means is of releasable type. This way, a given axial length of the piston rod can even be modified at a later stage, e.g. when the cartridge is subject to replacement.

Alternative and in another preferred embodiment, the gap size between the piston rod assembly and the piston or between the adjusting member and the piston is larger than zero. The distance between the piston and the piston rod assembly may range between 0.1 mm to 2.0 mm and is preferably less than 1 mm. In this embodiment, compensation of the gap is implemented into the drive mechanism of the drug delivery device.

In a further preferred aspect, the axial gap size between the piston rod assembly and the piston of the cartridge is modifiable by way of rotating the adjusting member and/or the piston rod relative to each other during assembly of the drug delivery device. In particular, the piston rod may be rotatably locked with respect to first and/or second housing components while the adjusting member is threadedly engaged with a distal end section of the piston rod. However, it is also conceivable, that both, adjusting member and piston rod are rotatably supported in the respective housing components.

In a further preferred embodiment, in particular in embodiments, wherein the axial gap size between piston rod assembly and piston is larger than zero, the drug delivery device further comprises a drive member which is releasably coupled to the piston rod and further comprises a resilient member which is arranged to move the drive member in the proximal direction with respect to the second housing component of the dose delivery, such that the piston rod is moved away from the piston by a pre-defined distance from a position of use, in which piston and piston rod assembly mutually abut, into an idle position, in which a pre-defined gap between the piston rod assembly and the piston of the cartridge is attained.

This has the advantage that a simple and precise usage of the drug delivery device is enabled. A user may administer a number of pre-set doses of the medicament. For example, when, after dose delivery, a force in the distal direction exerted on the drive member for dose delivery has been removed from the drive member, the drive member is moved in the proximal direction with respect to the housing due to the resilient member mechanically interacting with the drive member. The drive member may move in the axial direction with respect to the housing and/or rotate with respect to the housing. The proximal movement of the drive member may take place before the next dose is set. The piston rod may follow at least partly this movement of the drive member in the proximal direction. In particular, the drive member may be moved directly by the resilient member in the proximal direction with respect to the housing, whereas the piston rod may be moved indirectly by the resilient member via the movement of the drive member in the proximal direction with respect to the housing that is transferred to the piston rod. Thus, the piston rod may be moved relative to the piston in the proximal direction. Thereby, the distance between the piston rod and the piston may be increased. In this way, room is provided that allows a deformed piston, in particular an elastically deformed piston, to relax in the proximal direction after dose delivery.

Accordingly, after the piston rod has been moved proximally, the pressure exerted by the piston rod on the piston may be reduced or removed from the piston. Thus, the deformed piston may mainly relax in the proximal direction after dose delivery. Uncontrolled relaxation of the piston in the distal direction which may result in unintentionally dispensing fluid from the cartridge may thus be reduced. Furthermore, an increased distance between the piston rod and the piston before setting a subsequent dose may result in reducing the risk of a medicament being unintentionally dispensed from the cartridge, due to vibrations, for example, as the mechanical connection between piston and piston rod is interrupted.

Overall, the dose accuracy may be improved by moving the piston rod in the proximal direction after dose delivery. Preferably, the piston rod is moved in the proximal direction after dose delivery only as far as it is required for allowing relaxation of the piston in the proximal direction.

Preferably, the piston is moved in proximal direction in a well-defined idle position, wherein the distance between said idle position and a position of use, in which the piston rod assembly abuts with the piston of the cartridge, is entirely controlled and adjusted by the drive mechanism. Once the relative position between piston rod and adjusting member has been adjusted for the purpose of tolerance elimination, the piston rod assembly can even be axially displaced and may even be separated from the piston without introducing any supplemental tolerances.

Moreover, the drug delivery device according to the present invention is preferably designed as disposable device. Hence, during assembly, the first housing component is equipped with the cartridge filled with the medicament. In the final assembly of the drug delivery device, first and second housing components are interconnected in a permanent way, such that after consumption of the medicament the entire drug delivery device is intended to become discarded.

When the drug delivery device enters the sales market it is already provided with a medicament-filled cartridge and it is ready to use.

In another independent aspect, the invention also refers to a method of assembling a drug delivery device, wherein in a first step the cartridge being filled with the medicament is positioned in the first housing component to form a cartridge sub-assembly. Also, in a similar way, the drive mechanism that comprises the piston rod assembly is positioned in the second housing component to form a housing sub-assembly.

Thereafter, axial position of the piston is individually determined with respect to the first housing component, and in a corresponding way, also the axial position of the piston rod assembly is determined or measured. In particular the position of the distal end face of the piston rod assembly and/or the position of the proximal end face of the piston is determined with respect to the first and second housing components, respectively. Having determined or measured axial positions of the piston and the piston rod assembly with respect to their respective sub-assembly or housing component, the axial dimensions or axial elongation of the piston rod assembly is modified by moving the adjusting member relative to the piston rod, such that the axial distance between the piston and the piston rod assembly equals the pre-defined gap size when the drug delivery device is finally assembled, e.g. by interconnecting cartridge sub-assembly and housing sub-assembly. After having modified the relative axial position of adjusting member and piston rod, first and second housing components are mutually interconnected in a final step of assembly.

Typically, axial positions of piston and/or piston rod assembly are determined with respect to selected reference points of a respective cartridge or housing sub-assembly or with respect to reference points of respective first and/or second housing components. For instance, mutually corresponding connecting or fastening means of first and second housing components may serve as reference points for determining respective axial positions of the cartridge's piston and/or of the distal end face of the piston rod assembly. Measuring of the relative or absolute positions of piston and piston rod and/or of its adjusting member is conducted by way of tactile means and/or contactless, e.g. in an all-optical way.

In a further preferred embodiment, the axial position of the piston rod assembly and in particular the axial position of the adjusting member is modified when the piston rod or the piston rod assembly is in its position of use. Additionally, also determination or measuring of the axial position of the piston rod might be conducted with the piston rod, in particular the piston rod assembly being in its position of use. This way, any axial tolerances that might be due to the functionality of the drive mechanism to displace the piston rod between a position of use and an idle position are of no consequences and do not have to be considered.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compounds, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)-4-des Pro36, des Pro37 Exendin-4(1-39)-NH2,
H-(Lys)-5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)-6-des Pro36 [Asp28] Exendin-4(1-39)-Lys6-NH2,
des Asp28 Pro36, Pro37, Pro38Exendin-4(1-39)-NH2,
H-(Lys)-6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)-6-des Pro36, Pro37, Pro38 [Asp28] Exendin-4(1-39)-(Lys)6-NH2,
H-Asn-(Glu)-5-des Pro36, Pro37, Pro38 [Asp28] Exendin-4(1-39)-(Lys)6-NH2,
H-(Lys)-6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)-6-des Pro36, Pro37, Pro38 [Trp(O2)25, Asp28] Exendin-4(1-39)-NH2,
H-Asn-(Glu)-5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)-6-des Pro36, Pro37, Pro38 [Trp(O2)25, Asp28] Exendin-4(1-39)-(Lys)6-NH2,
H-Asn-(Glu)-5-des Pro36, Pro37, Pro38 [Trp(O2)25, Asp28] Exendin-4(1-39)-(Lys)6-NH2,
H-(Lys)-6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)-6-desPro36, Pro37, Pro38 [Met(O)14, Asp28] Exendin-4(1-39)-NH2,
H-Asn-(Glu)-5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)-6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)-6-des Pro36, Pro37, Pro38 [Met(O)14, Asp28] Exendin-4(1-39)-NH2,
H-Asn-(Glu)-5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)-6-des Pro36, Pro37, Pro38 [Met(O)14, Trp(O2)25, Asp28] Exendin-4(S1-39)-(Lys)6-NH2,
H-Asn-(Glu)-5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from its spirit and scope. Further, it is to be noted, that any reference signs used in the appended claims are not to be construed as limiting the scope of the present invention.

BRIEF DESCRIPTION OF THE DRAWINGS

Without limitation, the present invention will be explained in greater detail below in connection with preferred embodiments and with reference to the drawings in which.

DETAILED DESCRIPTION

Figure 1:
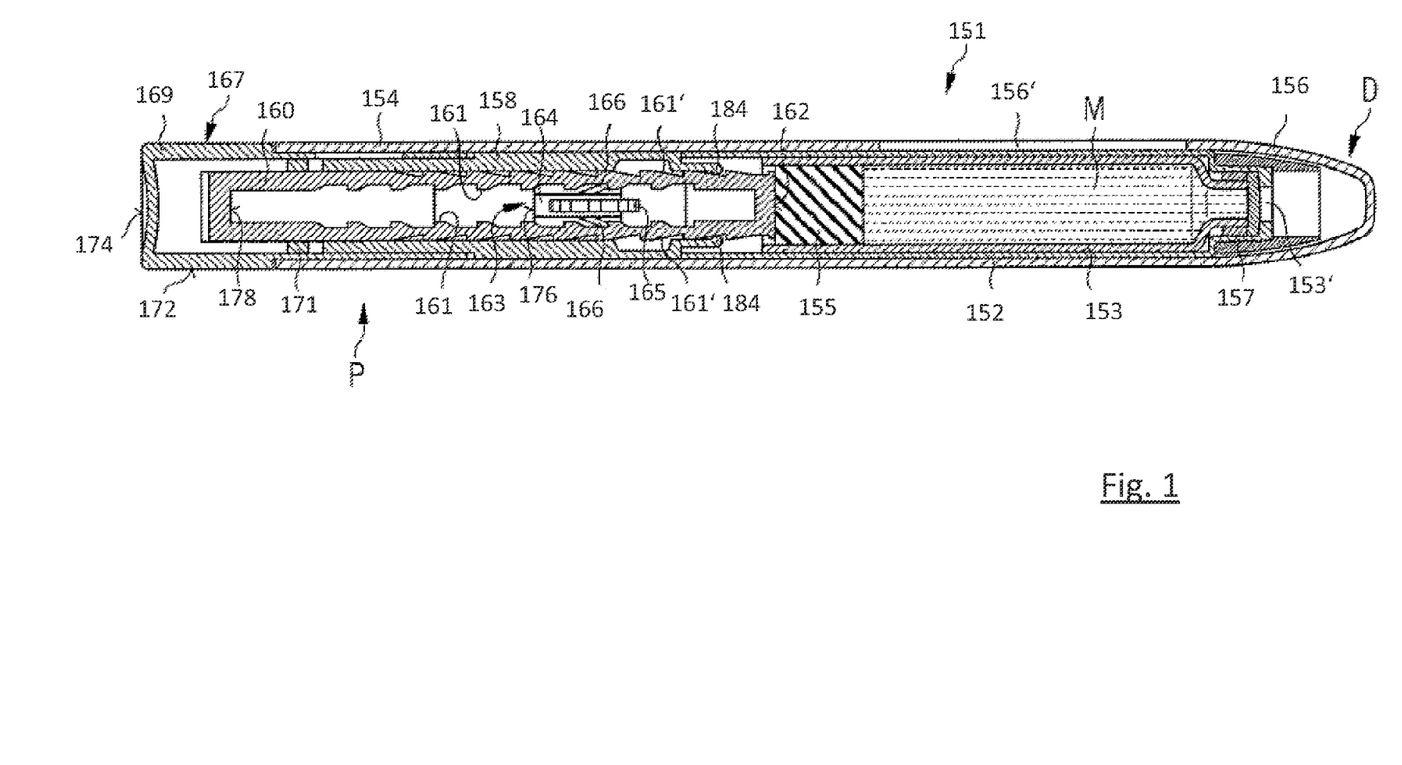
FIG. 1 shows a sectional view of an exemplary embodiment of a drug delivery device in a first, cartridge full, position.

The drug delivery device 151 comprises a cartridge housing 152 and a cartridge 153. The cartridge 153 is retained within the cartridge housing 152. The cartridge has an outlet 153'. The device 151 comprises a main (exterior) housing 154 having a proximal end P and a distal end, which is closest to the dispensing end D of the medication delivery device 1. The proximal end of the cartridge housing 152 and the distal end of the main housing 154 are secured together by any suitable means known to the person skilled in the art. In the illustrated embodiment, the cartridge housing 152 is secured within the distal end of the main housing 154.

The cartridge 153 from which a number of doses of a medicament M may be dispensed is provided in the cartridge housing 152. A piston 155 is retained in the proximal end of the cartridge 153. A removable cap 156 is releasably retained over the distal end of the cartridge housing 152. The removable cap 156 may be optionally provided with one or more windows to the cartridge 156' through which the position of the piston 155 within the cartridge 153 can be viewed.

In the illustrated embodiment, the distal end of the cartridge housing 152 is provided with a distal threaded region 157 designed for the attachment of a suitable needle assembly to enable medication to be dispensed from the cartridge 153. In the illustrated embodiment, the main housing part 153 is provided with an insert, i.e. internal housing 158. The internal housing 158 is secured against rotational and axial movement with respect to the main housing 154. Alternatively, the internal housing 158 may be formed integrally with the main housing 154. Additionally, the internal housing 158 is provided with a plurality of guide lugs (not illustrated) and pawl means 184 (cf. FIG. 1). The pawl means 184 may be an integrated part of the internal housing 158 or may be a separate component.

A piston rod 160 extending through the main housing 154 has a first set of indentations 161' extending longitudinally along external surfaces of the piston rod 160. In particular, the piston rod 160 is designed and arranged to be secured against rotational movement with respect to the main housing 154. A second set of indentations 161 extends longitudinally along internal surfaces of the piston rod 160. The first set of indentations 161' of the piston rod 160 extends through and is engaged with the pawl means 184 provided on the internal housing 158 to prevent movement of the piston rod 160 in the proximal direction with respect to the housing during setting of the dose. A bearing surface 162 located at the distal end of the piston rod 160 is disposed to abut a proximal face of the piston 155. In the illustrated embodiment the longitudinal spacing of the first set of indentations and the second set of indentations 161 is essentially equal.

A pinion gear 163, consisting of a carrier 164 and a pinion 165, free to rotate within the carrier 164, is located within a channel within the piston rod 160. Pawl arms 166 located on the carrier 164 are releasably engaged with the second set of indentations 161 of the piston rod 160. The pawl arms 166 of the carrier 164 are designed to transmit force to the piston rod 160 in the distal direction during dispense and to allow relative movement between the pinion gear 163 and the piston rod 160 in the proximal direction during setting the dose. The teeth of the pinion 165 may be permanently engaged with teeth of a second rack (not illustrated) of the internal housing 158.

A drive member 167 extends about the piston rod 160 and is releasably coupled to the piston rod 160. The drive member 17 comprises a rack part and an activation part 169. The rack part and the activation part 169 are secured to each other to prevent rotational and axial movement there between. Alternatively, the drive member 167 may be a unitary component consisting of an integrated rack part and activation part 169.

The rack part is provided with a first rack extending along the main axis of the rack part. The teeth of the first rack of the rack part are permanently engaged with the teeth of the pinion 165.

The drive member 167 has a plurality of guide slots (not shown) in which the guide lugs of the internal housing 158 are located. These guide slots define the extent of permissible axial movement of the drive member 167 with respect to the housing 154. In the illustrated embodiment the guide slots also prevent rotational movement of the drive member 167 relative to the main housing 154.

The drug delivery device 151 further comprises a resilient member 171. The resilient member 171 is arranged to move the drive member 167, preferably to move the drive member 167 and the piston rod 160 together, in the proximal direction with respect to the main housing 154 after dose delivery, thereby reducing or even removing pressure of the piston rod 160 on the piston 155. The resilient member 171 is arranged to mechanically interact with the drive member 167 at a distal end side of the drive member 167. In this exemplary embodiment, the resilient member 171 is formed integrally with the internal housing 158. Alternatively, the resilient member 171 may be formed integrally with the main housing 154. In another embodiment, the resilient member may be an element separate from the housing and from the internal housing. For example, the resilient member 171 is a spring, for instance a circular spring, a leaf spring or a coil spring.

The activation part 169 of the drive member 167 has a plurality of grip surfaces 172 and a dispensing face 174. To increase intuitiveness of the operation of the medication delivery device 151 and to indicate visual feedback regarding dose setting, the main housing 154 may optionally be provided with a window to the drive member through which graphical status indicators provided on the drive member 167 can be viewed.

In the following, the operation of the drug delivery device 151 will be described.

To set a dose a user grips the grip surfaces 172 of the drive member 167. The user then pulls the drive member 167 in a proximal direction away from the main housing 154 thereby moving the rack part in a proximal direction. The proximal movement of the rack part causes the pinion 165 to rotate and move proximally by virtue of the engagement of the teeth of the pinion 165 of the pinion gear 163 with the teeth of the first rack of the rack part and the teeth of the second rack of the internal housing 158 thus moving the pinion gear 163 in the proximal direction.

The piston rod 160 is prevented from moving proximally by interaction of pawl means 184 of the internal housing 158 with the first set of indentations 161' on the piston rod 160 during dose setting. As the drive member 167 travels in the proximal direction relative to the piston rod 160, the pawl arms 166 of the carrier 164 are elastically displaced inwardly by interaction with the second set of indentations 161 of the piston rod 160.

Figure 2:
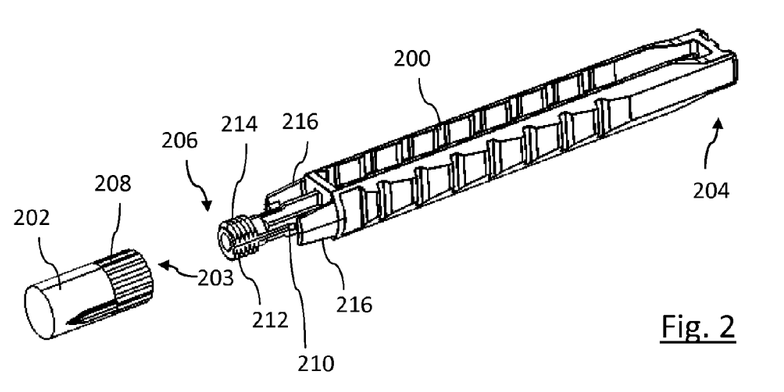
FIG. 2 shows a perspective and isolated illustration of the piston rod assembly with an adjusting member disassembled from the piston rod.
Figure 3:
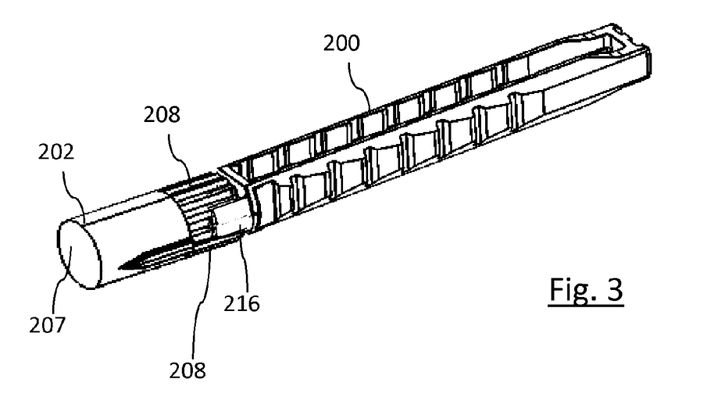
FIG. 3 shows the piston rod assembly according to FIG. 2, wherein adjusting member and piston rod are mutually assembled.

The proximal travel of the drive member 167 is limited by the guide slots of the rack part. At the end of the travel of the drive member 167, the pawl arms 166 of the carrier 164 engage with the next sequential indentation of the second set of indentations 161 of the piston rod 160 as indicated in FIG. 2. The action of the pawl arms 166 of the carrier 164 positively engaging the second set of indentations 161 of the piston rod 160 creates an audible and tactile feedback to the user to indicate that the dose has been set.

When the dose has been set, the user may then dispense this dose by depressing the dispensing face 174 of the activation part 169 of the drive member 167. By this action the drive member 167 and the rack part are moved axially in the distal direction relative to the main housing 154. As the teeth of the pinion 165 of the pinion gear 163 are engaged with the teeth of the first rack of the rack part and the teeth of the second rack of the internal housing 158, the pinion 165 of the pinion gear 163 is caused to rotate and move in the distal direction thus moving the pinion gear 163 longitudinally in the distal direction. As the pawl arms 166 of the carrier 164 of the pinion gear 163 are engaged with the second set of indentations 161 of the piston rod 160, the piston rod 160 is caused to move longitudinally in the distal direction with respect to the internal housing 158.

The distal axial movement of the piston rod 160 causes the bearing surface 162 of the piston rod 160 to bear against the piston 155 in the cartridge 153 causing the piston 155 to be deformed and moved distally, thereby causing a dose of medicament to be dispensed through the attached needle (not explicitly shown).

The distal travel of the drive member 167 is limited by the guide slots (not explicitly shown) of the rack part. Audible and tactile feedback to indicate that the dose has been dispensed is provided by the interaction of the pawl means 184 of the internal housing 158 with the first set of indentations 161' of the piston rod 160. Additionally, visual feedback regarding dose dispense may optionally be indicated by a graphical status indicator, provided on the drive member 167, which can be viewed through the optional window to the drive member in the main housing 154.

When the drug delivery device 151 is in a condition where the maximum number of doses has been delivered, a proximal face 176 of the carrier 164 abuts an internal distal face 178 of the piston rod 160 to prevent further axial movement of the pinion gear 163 and thus the drive member 167 in proximal direction.

Further doses may be delivered as required up to a predetermined maximum number of doses. After distal movement of the drive member 167 for dose delivery is finished, the resilient member 171 has been biased. For example, a distal end face of the drive member may have moved into abutment with the resilient member 171 and the drive member 167 may have been moved further into the distal direction together with the resilient member 171, thereby biasing the resilient member 171. After the user removes the force acting on the drive member 167 in the distal direction, the biased resilient member 171 moves the drive member 167 and the piston rod 160 in the proximal direction with respect to the main housing 154. Thereby, pressure of the piston rod 160 on the piston 155 is reduced as the piston rod is retracted from the piston. In this way, room for relaxation of the piston in the proximal direction may be provided. Relaxation of the piston 155 in the distal direction may be reduced or avoided in this way. Correspondingly, unintentional weeping of the device may be reduced.

Preferably, the piston rod 160 is moved away from the piston 155 by a distance and/or the drive member 167 is moved by a distance in the range of (about) 0.1 to 2.0 mm, in particular in the range of (about) 0.1 to 0.5 mm, in the proximal direction with respect to the main housing 154 by means of the resilient member 171 moving the drive member 167 in the proximal direction after dose delivery. The distance the drive member 167 is moved does not have to be the same as the distance the piston rod 160 is moved, i.e. the piston rod 160 and the drive member 167 may be coupled with mechanical advantage.

The drive mechanism illustrated and described in FIG. 1 is only exemplary and only provides one of a variety of drive mechanisms that can be used with the piston rod assembly according to the present invention.

The piston rod 200 as illustrated in FIG. 2 slightly differs from the piston rod 160 as illustrated in FIG. 1. In FIGS. 2 through 5, the length adjusting feature of the piston rod assembly is exemplary illustrated. The piston rod 200 comprises a socket portion 210 at its distal end section. The socket portion 210 is designed as a centrally located and distally extending stud having a threaded head 212 at its free end pointing towards the distal direction.

Here, the distally located head 212 comprises an outer thread 214. With its opposite, proximal end section 204, the piston rod 200 is operably engaged with the drive mechanism as exemplary illustrated in connection with FIG. 1.

The adjusting member 202 is designed as a cupped receptacle. It is of substantially hollow cylindrical shape and comprises a receptacle having an opening facing towards the proximal direction. Hence, the adjusting member 202 is adapted to threadedly receive the head 212 of the piston rod's socket portion 210.

Figure 4:
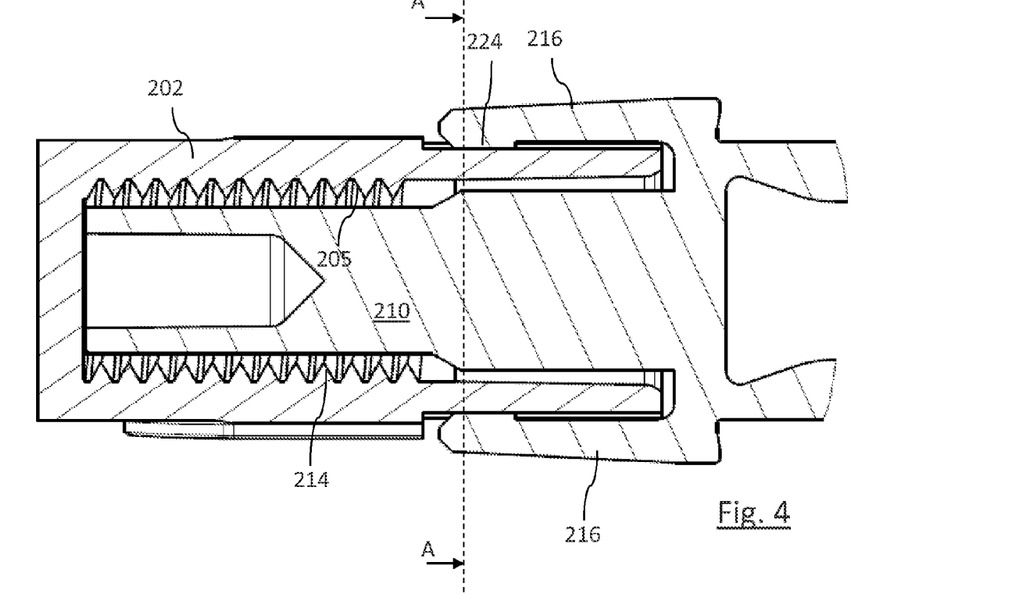
FIG. 4 shows a longitudinal cross section of the piston rod according to FIG. 3.

As further illustrated in FIG. 4, the receptacle 203 of the adjusting member 202 comprises an inner thread 205 corresponding and matching with the outer thread 214 of the head 212 of the socket portion 210 of the piston rod 200. At its distal end face directed towards a piston of the cartridge, the adjusting member 202 comprises a contact surface 207, which is substantially planar. By way of the contact surface 207, the adjusting member may but against a proximal end face of the piston 155, preferably across its entire cross section or surface 207.

By way of the threaded engagement of adjusting member 202 and piston rod 200, the overall axial length of the piston rod assembly can be continuously modified in order to reduce or even to annihilate inevitable production and/or assembly tolerances of the drug delivery device 151.

In order to inhibit self-acting relative rotation of adjusting member 202 relative to the piston rod 200, the piston rod 200 further comprises axially extending tongue members 216 comprising radially inwardly protruding lug portions 224 at least at their distal end section. Since the tongue members 216 are arranged laterally offset from the centrally located socket portion 210, a circumferential gap is formed between said tongue members 216 and the socket portion 210. The size of this circumferential gap is sufficient to receive the cylindrical side wall of the adjusting member 202.

Figure 5:
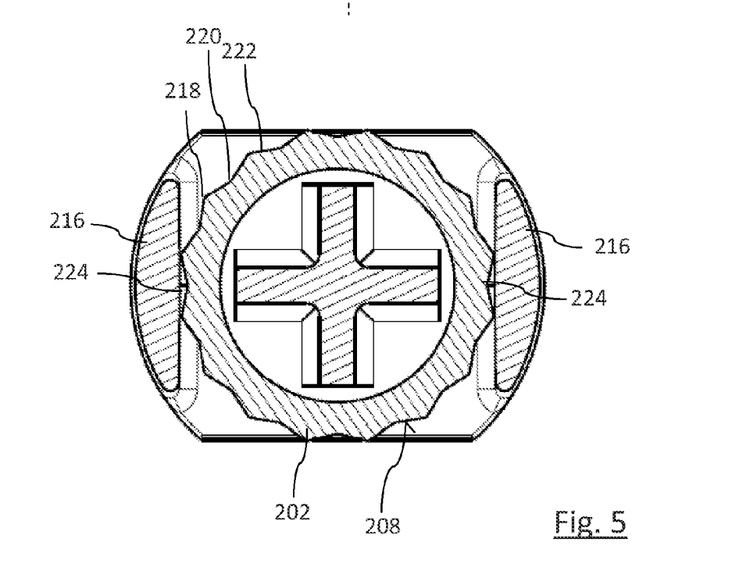
FIG. 5 shows a cross section along A-A according to FIG. 4.

In order to provide a kind of snap-in functionality, the adjusting member 202 comprises a corrugated outer surface 208 at its proximal end section. Preferably, the corrugations or elongated ribs extend in longitudinal or axial direction. As illustrated in FIG. 5, the corrugations may comprise ridge sections 218 and bottom sections 220 regularly and periodically arranged along the outer circumference of the side wall of the adjusting member 202. Between elevated ridge sections 218 and recessed bottom sections 220, here, a substantially straight flank or side section 222 extends.

The lug portion 224 extending radially inwardly at the tongue members 216 typically matches with the profile of the corrugated surface 208 of the adjusting member 202. Since the tongue members 216 are resiliently biased with respect to the piston rod 200, they can be elastically bended radially outwardly and thus allow to rotate the adjusting member 202 with respect to the piston rod 200.

However, once a pre-defined axial position of the adjusting member has been reached, the positive and/or frictional engagement of the tongue members 216 and the corrugated surface 208 of the adjusting member 202 prevents and inhibits any further self acting rotation of the adjusting member 202 relative to the piston rod 200. This way, mutual engagement of tongue members 216 and adjusting member 202 provides a self-locking or self-inhibiting threaded engagement of piston rod 200 and adjusting member 202.

The invention claimed is:

1. A piston rod assembly for a drug delivery device, comprising: a piston rod adapted to be operably engaged with a piston of a cartridge containing a medicament, at least one adjusting member displaceably disposed at the piston rod with respect to the piston rod's long axis, and being interconnected with a distal end section of the piston rod, and at least one interlock means adapted to interact with the adjusting member and with the piston rod for mutually locking in position the adjusting member and the piston rod in an arbitrary relative position and wherein the adjusting member and the piston rod are threadedly engaged in order to axially displace the piston rod and the adjusting member relative to each other, and wherein the interlock means is inhibits self-acting relative rotation between the piston rod and the adjusting member, wherein the interlock means comprise at least one resiliently biased tongue member adapted to engage with a corrugated outer surface portion of the adjusting member or of the piston rod.

2. The piston rod assembly according to claim 1, wherein the adjusting member comprises a cupped receptacle adapted to receive a correspondingly threaded distal socket portion of the piston rod.

3. The piston rod assembly according to claim 2, wherein the tongue member is arranged laterally offset with respect to the socket portion.

4. The piston rod assembly according to claim 2, wherein a radially inwardly facing side wall section of the receptacle is threaded and wherein an outwardly facing side wall section of the receptacle is corrugated or vice versa.

5. The piston rod assembly according to claim 2, wherein threaded and corrugated side wall sections of the receptacle are arranged at least partially offset in axial direction.

6. The piston rod assembly according to claim 4, wherein the piston rod comprises two tongue members axially displaced with respect to the piston rod's distal end section, and wherein the tongue members comprise radially inwardly pointing lug portions adapted to engage with the corrugated outer side wall section of a proximal end section of the adjusting member.

7. The piston rod assembly according to claim 1, wherein the adjusting member comprises a contact surface at its distal end section facing towards a proximal end section of the piston in an assembly configuration.

8. A drug delivery device for dispensing of a dose of a medicament, comprising, a first housing component for a cartridge comprising a medicament, wherein the cartridge comprises a piston slidably arranged therein in an axial direction, a second housing component housing a drive mechanism comprising the piston rod assembly according to claim 1, wherein the first and the second housing components are adapted to be interlocked by way of mutually corresponding fastening means, and wherein the piston rod assembly is adapted to modify an axial gap between the piston rod assembly and the piston to a predefined gap size, wherein the axial gap size between the piston rod assembly and the piston is modifiable by way of a threaded engagement of the adjusting member and the piston rod in order to axially displace the piston rod and the adjusting member relative to each other.

9. The drug delivery device according to claim 8, wherein the axial gap size between the piston rod assembly and the piston is modifiable by way of rotating the adjusting member and the piston rod relative to each other during assembly of the drug delivery device.

10. The drug delivery device according to claim 8, further comprising a drive member being releasably coupled to the piston rod and having further a resilient member which is arranged to move the drive member in the proximal direction with respect to the second housing component after dose delivery, such that the piston rod is moved away from the piston by a predefined distance from a position of use into an idle position.

11. A method of assembling a drug delivery device according to claim 8, comprising the steps of:
positioning the cartridge being filled with the medicament, in the first housing component to form a cartridge sub-assembly,
positioning the drive mechanism comprising the piston rod assembly in the second housing component to form a housing sub-assembly,
determine the axial position of the piston with respect to the first housing component,
determining the axial position of the piston rod assembly with respect to the second housing component,
modifying the axial dimensions of the piston rod assembly by moving the adjusting member relative to the piston rod such that the axial distance between the piston and the piston rod assembly equals the predefined gap size when the drug delivery device is finally assembled,
mutually interconnecting first and second housing components.

12. The method according to claim 11, wherein the axial position of the piston rod assembly is measured with respect to at least one reference point of the second housing component when piston rod is in its position of use.

13. The method according to claim 11, wherein the axial dimensions of the piston rod assembly is modified when the piston rod is in its position of use.

* * * * *